United States Patent [19]

Brown

[11] 4,427,116

[45] Jan. 24, 1984

[54] DENITRIFICE ENCAPSULATION

[76] Inventor: Walter L. Brown, 2630 Wagon Dr. #3B, Alexandria, Va. 22303

[21] Appl. No.: 346,742

[22] Filed: Feb. 8, 1982

[51] Int. Cl.³ ............................................. B65D 85/56
[52] U.S. Cl. .................................. 206/530; 206/63.5; 132/84 D; 424/37; 424/49
[58] Field of Search .............. 206/530, 484, 581, 63.5; 132/84 B, 84 D; 426/115, 138; 424/31, 37, 49

[56] References Cited

U.S. PATENT DOCUMENTS

| | | | |
|---|---|---|---|
| 1,134,156 | 4/1915 | Planten | 424/37 |
| 1,364,188 | 1/1921 | Draenert | 132/84 B |
| 1,637,153 | 7/1927 | Lawton | 206/63.5 |
| 1,955,175 | 4/1934 | Crowther | 206/63.5 |
| 2,031,233 | 2/1936 | Stillwell et al. | 424/49 |
| 2,176,308 | 10/1939 | Larkin | 206/63.5 |
| 3,536,074 | 10/1970 | Aufhauser | 206/219 |
| 3,593,725 | 7/1971 | Ortega et al. | 132/84 B |
| 3,865,603 | 2/1975 | Szymanski et al. | 206/530 |
| 4,105,120 | 8/1978 | Bradberry | 206/581 |
| 4,325,761 | 4/1982 | Pace | 206/530 |

*Primary Examiner*—William T. Dixson, Jr.
*Assistant Examiner*—Brenda J. Ehrhardt

[57] ABSTRACT

A prdetermined amount of toothpaste sufficient for a single brushing of the teeth is encapsulated with a covering which is easily storable, non-toxic and easily breakable when chewed or bitten.

1 Claim, No Drawings

DENTIFRICE ENCAPSULATION

BACKGROUND OF THE INVENTION

1. Field of the Invention

This invention relates to the compact packaging of toothpaste and more specifically to the encapsulation of an amount of toothpaste sufficient to provide for a single brushing of the teeth.

2. Description of the Prior Art

The most general types of toothpaste storage containers include various size tubes fabricated of flexible wall materials. A number of problems arise with the use of tubes for storing toothpaste. The tubes have a tendency to split, are easily punctured, do not release all the stored toothpaste, are cumbersome to store and to carry on travel, hiking, camping, picnics, etc., the caps are too easily lost and there is a tendency to waste toothpaste indiscriminately by not being able to accurately control or stop the flow of the toothpaste from the tube during use.

SUMMARY OF THE INVENTION

The general purpose of this invention is to eliminate the above noted problems by prepackaging, an individual containers, essentially only the amount of toothpaste one would need for a single brushing of the teeth.

DESCRIPTION OF THE INVENTION

It has been found that toothpaste can be packaged in very small amounts for ease of handling, storage and use.

The toothpaste could be made available in various flavors for improving the marketability and for affording the user a varying selection. Numerous sizes, colors, designs and shapes may be used to encourage children to brush regularly and effectively.

The encasing means for the toothpaste may take any of several different forms and may be made of a material which retains its shape to some extent and can be easily handled, stored and dispensed. One particularly effective encasement has been found to be gelatin capsules, but a number of other suitable means are also available. The major criteria for selecting a material for encapsulating the toothpaste essentially consists of: preferably a soft covering, soluble in water, compatible with the tooth cleaning product, non-toxic and easily breakable when chewed or bitten. The covering should preferably be made from a non-sugar containing material, but this selection would be made strictly on the basis of preference. The general opinion exists of "reduction of sugar results in corresponding reduction of tooth decay." Upon use of the encapsulated toothpaste, one only has to gently apply pressure with the teeth to capsule for the release of the toothpaste into the mouth and upon removal of the outer coating (where a non-dissolving coating has been used), the teeth may be brushed as usual.

Various types of covering and techniques for encapsulation have been found to include the use of gelatin capsules having an imperviousness to aqueous solutions containing less than ten percent water but which will readily dissolve in a liquid environment, such as the mouth. The toothpaste may be fed into the gelatin capsule or a measured amount of toothpaste may be covered with a thin coating of gelatin or like material.

Many variations of the above structures will be immediately obvious to those skilled in the art but the invention is to be limited only by the appended claims.

I claim:

1. A capsule containing a predetermined amount of toothpaste encapsulated in a non-toxic, semi-soluble gelatin material, said capsule being rupturable and adapted to be ruptured by the teeth when placed within the mouth of a user, thereby releasing a sufficient amount of toothpaste for a single brushing of the teeth, said capsules being gelatin material having an imperviousness enclosing said toothpaste having an aqueous content of less than ten percent water but which readily dissolves within the higher liquid environment of the mouth.

* * * * *